United States Patent [19]

Hartmeier

[11] Patent Number: 4,460,686
[45] Date of Patent: Jul. 17, 1984

[54] GLUCOSE OXIDATION WITH IMMOBILIZED GLUCOSE OXIDASE-CATALASE

[75] Inventor: Winfried Hartmeier, Ingelheim am Rhein, Fed. Rep. of Germany

[73] Assignee: Boehringer Ingelheim GmbH, Ingelheim am Rhein, Fed. Rep. of Germany

[21] Appl. No.: 373,291

[22] Filed: Apr. 29, 1982

Related U.S. Application Data

[63] Continuation of Ser. No. 126,033, Feb. 29, 1980, abandoned.

[30] Foreign Application Priority Data

Mar. 22, 1979 [DE] Fed. Rep. of Germany ....... 2911192

[51] Int. Cl.³ .................... C12P 7/58; C12N 11/18; C12N 11/02
[52] U.S. Cl. .................................. 435/137; 435/175; 435/177
[58] Field of Search .............. 435/137, 174, 175, 176, 435/177, 190, 94

[56] References Cited

U.S. PATENT DOCUMENTS 3,050,444  8/1962  Holstein et al. ...................... 435/94
3,841,971 10/1974  Messing ............................... 435/175
3,843,446 10/1974  Vieth et al. ...................... 435/175 X
3,935,071  1/1976  Bergmeyer et al. ................. 435/137
3,996,107 12/1976  Martensson ...................... 435/175 X
4,033,817  7/1977  Gregor ............................. 435/175 X
4,039,382  8/1977  Thang et al. ........................ 435/175
4,102,745  7/1978  Thompson et al. ............. 435/175 X

OTHER PUBLICATIONS

Messing, R. A., Immobilized Glucose Oxidase and Catalase in Controlled Pore Titania, Immobilized Enzymes in Food and Microbial Processes, Plenum Press, N.Y., 1974 (pp. 149-156).

Primary Examiner—David M. Naff
Attorney, Agent, or Firm—Hammond & Littell, Weissenberger & Dippert

[57] ABSTRACT

Economical oxidation of glucose is achieved by oxidation with an immobilized glucose oxidase-catalase composition in a reaction mixture at low temperatures below 15° C., preferably between 10° C. and the freezing point of the reaction mixture. The immobilized glucose oxidase-catalase composition preferably contains glucose oxidase and catalase bonded to hardened protein particles with the catalase activity being at least one-sixth of the glucose oxidase activity.

1 Claim, 1 Drawing Figure

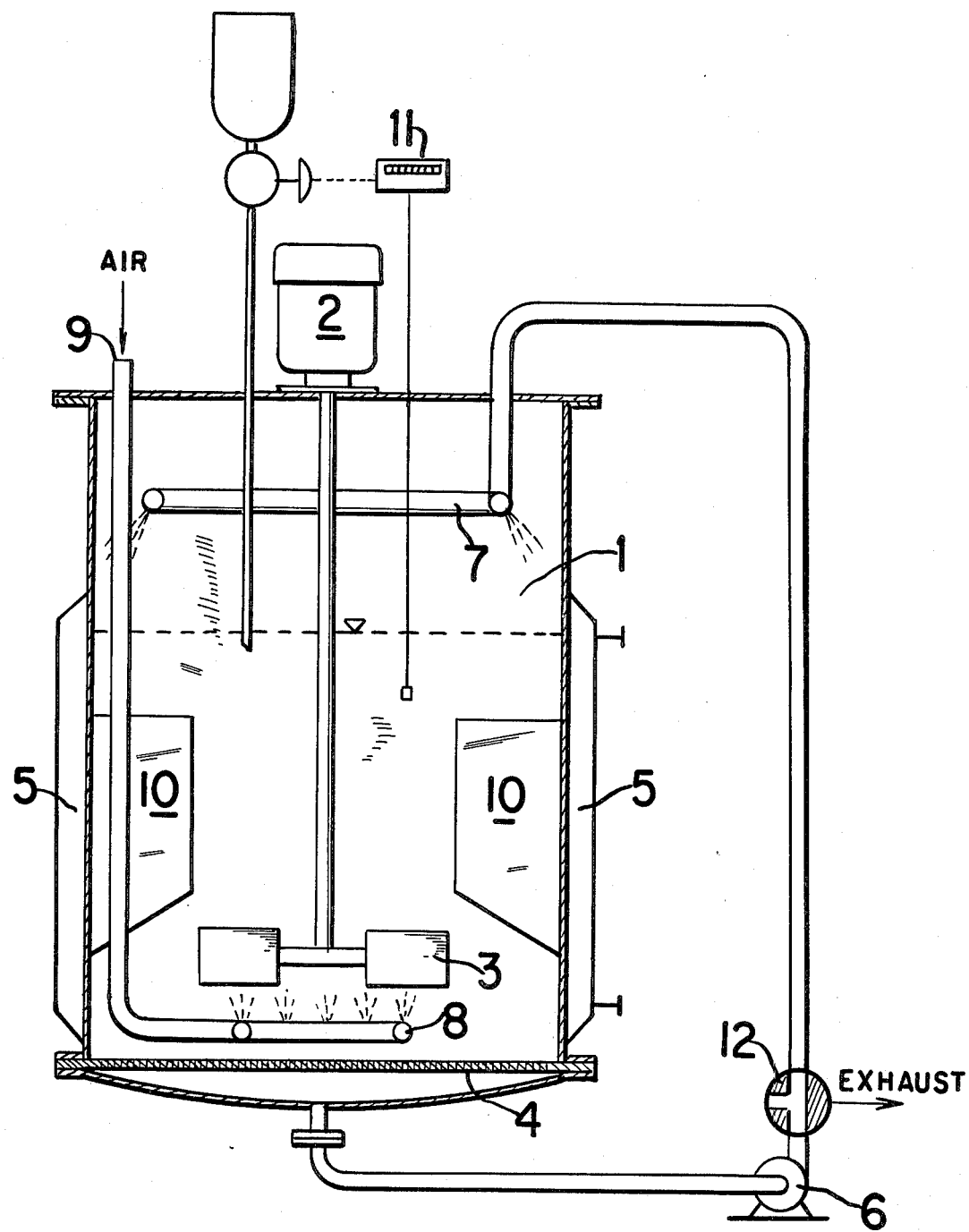

GLUCOSE OXIDATION WITH IMMOBILIZED GLUCOSE OXIDASE-CATALASE

This is a continuation of copending application Ser. No. 126,033, filed Feb. 29, 1980, now abandoned.

This invention relates to a novel particle-bound, water-insoluble glucose oxidase-catalase composition having a definite minimum catalase activity, as well as to a method of using the same for glucose oxidation at low temperatures.

BACKGROUND OF THE INVENTION

It is known to oxidize glucose enzymatically in aerated agitator reactors by means of an enzyme mixture consisting of glucose oxidase (GO) and catalase (CAT). In this process, the enzyme mixture (GO-CAT) effects an oxidation of glucose into glucono-δ-lactone, which converts in an aqueous solution, as a rule spontaneously or catalyzed by lactonase, into gluconic acid in accordance with the following equation:

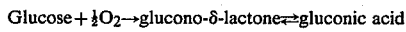

Glucose + ½O$_2$ → glucono-δ-lactone ⇌ gluconic acid

More particularly, the two individual enzymes GO and CAT effect the course of reaction by means of the following successive steps:

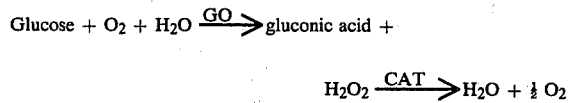

Glucose + O$_2$ + H$_2$O $\xrightarrow{GO}$ gluconic acid +

H$_2$O$_2$ $\xrightarrow{CAT}$ H$_2$O + ½ O$_2$

When catalase is present, as it normally is in many technical GO-compositions, the intermediate formed hydrogen peroxide is split, so that, as a rule, no noticeable accumulation of hydrogen peroxide in the reaction medium occurs. Thus, the reaction proceeds predominantly in accordance with the above first-mentioned equation. In the technical and patent literature, however, little attention is paid to the catalase content; the catalase component is often not mentioned, and instead only the glucose oxidase is mentioned.

Industrial use of soluble GO-CAT mixtures has already been made for a long time by the food industry for removal of glucose or oxygen traces from food or beverages. Thus, soluble GO-CAT, for example, is mixed into egg products in order to remove traces of glucose from them. A further frequent use is in the soft drink sector. There, the GO-CAT mixture added to the beverage serves to remove oxygen, and thus prevents damage by oxidation. GO has also found wide use as an analytical auxiliary, for example, for glucose determination.

In contrast to the above-mentioned fields of use, GO-CAT has found no use or only spotty practical use for technical glucose oxidation. U.S. Pat. No. 3,050,444 discloses a process where glucose contained in invert sugar (=glucose+fructose—mixtures) is oxidized with the aid of soluble GO-CAT. The formed gluconic acid may be separated substantially more easily from the fructose, for example by precipitation such as its calcium salt than the originally present glucose. In the United States the process was practised on a large technical scale in the sixties. However, because of the relatively high price of GO-CAT, it is today no longer competitive.

In order to compensate for the high price of enzymes, it was proposed in German Auslegeschrift No. 2,003,732 to recover the GO by electrodialysis from the reaction solution, and to use it then repeatedly in soluble form. According to this German Auslegeschrift, 830 gm of sodium gluconate could be prepared with 0.688 gm of commercial soluble GO, that is, with 1 gm of soluble GO 1206 gm of sodium gluconate may be obtained pursuant to this process. However, this process has a considerable disadvantage in that the electrodialysis needs complicated apparatus which, in industrial practice on a large scale, can hardly be mastered. The required multiple membrane dialysis devices are subject to damage and break-down.

Since immobilized (carrier fixed) enzyme preparations, and among these also immobilized GO and CAT, have been for years part of the state of the art, the idea of using immobilized preparations also for enzymatic glucose oxidation appears to be obvious. However, up to now no economical process useful on an industrial scale on the basis of immobilized GO and CAT could be developed. On the contrary, from the great number of publications in this field, it is obvious, that, up to now, the durability of such preparations under conditions prevailing in practice amounts to only a few days. Publications of this type are:

R. Carter, J. E. Prenosil & J. R. Bourne: A Deactivation Study of the Immobilized Glucose Oxidase/Catalase System.—First Europ. Congr. Biotechnol.,—Preprints, Part 1, pages 107–108, Interlaken, 1978.

K. Buchholz & M. Reuss: Kopplung von Stofftransport, Reaktion und Desaktivierung bei traegergebundener Glucoseoxidase und Katalase.—Chimia 31, 27–30 (1977).

K. Buchholz & B. Gödelmann: Macrokinetics and Operational Stability of Immobilized Glucose Oxidase and Catalase.—Biotechnol. Bioengineering 20, 1201–1220 (1978).

K. B. Ramachandran & D. D. Perlmutter: Effects of Immobilization on the Kinetics of Enzyme-Catalyzed Reactions. I. Glucose Oxidase in a Recirculated Reactor System.—Biotechnol. Bioengng. 18, 669–684 (1976).

S. Krishnaswamy & J. R. Mittrell: Deactivation Studies of Immobilized Glucose Oxidase.—Biotechnol. Bioengng. 20, 821–835 (1978).

A certain but still insufficient improvement of stability of the immobilized GO and CAT preparations could be achieved, according to several of the above-mentioned publications, by additionally using carrier materials which enhance the peroxide splitting, such as manganese oxide or ruthenium compounds. The half-life time of these preparations, that is, the time required for activity decrease to half of its original value, is also limited to several days at 25° to 35° C., the proposed reaction conditions mostly used in biotechnology. The concurrent use of inorganic catalysts, such as manganese oxide, is also questionable with respect to the food law.

OBJECTS OF THE INVENTION

It is an object of the present invention to enhance the total quantity of glucose reaction per unit weight of GO used, over that achievable pursuant to the prior art. According to German Auslegeschrift No. 2,003,732, the reacted total quantity of glucose heretofore amounted to about 1200 gm of glucose per 1 gm of commercial GO preparation. Furthermore, it is another object of the invention to simplify the process with respect to technical apparatus and to render it compatible with respect to the food law.

DESCRIPTION OF THE INVENTION

I have discovered that the above objects are achieved by using an immobilized glucose-oxidase-catalase preparation, both enzymes of which are each bonded in or to the same particle, and the catalase activity of which, expressed in Baker units, is at least one sixth of the glucose-oxidase activity, expressed in Sarrett units.

Furthermore, it has proved to be of advantage to carry out the oxidation reaction by means of the particle-bound enzymes described above at temperatures below 15° C., especially at temperatures between 10° C. and the freezing point of the reaction mixture. These exceptionally low temperatures, which are unusual for biotechnical reactions, assure very economical operation.

Immobilization of the glucose oxidase and catalase, that is, their fixing to carrier particles insoluble in water, may be effected pursuant to a known process. However, preparations such as have been used, for example, in the work of Buchholz et al. cited above, are unsuitable because catalase and glucose oxidase were there each bonded to different particles. In contrast thereto, for carrying out the process according to the present invention it is indispensable that glucose oxidase and catalase are each bonded in or to the same water-insoluble particle. Bonding of the two enzymes may be effected simultaneously or successively. It is important that the glucose oxidase and the catalase in the enzyme preparation are in as close proximity as possible to one another. The process described in German Auslegeschrift No. 2,636,206, for example, is well suited for this immobilization. According to that process, the enzymes are bonded to carrier particles of high molecular, porous, formaldehyde-hardened protein, such as gelatin, which has a water absorption capacity of 2 to 8 times its dry weight, and where the fixing is effected preferably by means of glutar-dialdehyde. Particle sizes between 10 and 100 μm have proved to be especially favorable.

As mentioned before, the catalase activity in the enzymatically active particles, expressed, in Baker units, must amount to at least one-sixth, but preferably one-fourth of the glucose oxidase activity, expressed in Sarett units. While, pursuant to present knowledge, less than the mentioned catalase proportion also suffices to prevent an accumulation of hydrogen peroxide in the reaction medium, I have found that an optimum reaction of glucose is reached only if the mentioned minimum catalase proportion is present. Of course, the catalase proportion may be, if desired, substantially greater than the mentioned smallest proportion. For economical reasons, however, it should not be higher, expressed in Baker units, than the gluxose oxidase content, expressed in Sarett units.

Besides the conventional carrier materials, splitting catalysts may also be used as carriers for the bound enzymes. However, the process according to the invention is not restricted to the use of enzymes immobilized on such carriers. As a rule, the use of enzymes with such carriers has to be foregone for food law considerations.

According to a further embodiment of the invention, other enzymes besides glucose oxidase and catalase may also be used in soluble or immobilized form for the process according to the invention. For example, glucose may be liberated by amylolytical enzymes from dextrin or starch, which is then further reacted by the glucose oxidase-catalase system.

In a preferred embodiment of the process according to the invention, 500 to 5000 Sarett units of glucose oxidase and 200 to 2000 Baker units of catalase per liter of reaction liquid are used in the immobilized form, that is, bound to water-insoluble particles of organic carrier material, as explained above.

The glucose concentration in the reaction medium may vary within wide limits. As a rule, it lies between 0 and 40 gm per 100 ml. Higher concentrations are possible, but they decrease the transfer of oxygen and thus the glucose reaction rate which depends upon the oxygen concentration in the reaction medium, while promoting the decrease by an increased glucose concentration.

As is generally conventional in processes of this kind, the agitator reactor is aerated with oxygen or with an oxygen-containing gas, such as air. The aeration rate amounts normally to 0.1 to 2.0 volumes of gas under normal pressure per 1 volume reaction medium per minute. For example, 1000 liter of fermentation liquid are aerated with 1 $m^3$ of air under normal pressure and temperature per minute. Oxygen supply with addition of hydrogen peroxide proved to be unsuitable for the performance of the process according to the invention because the enzymes are inactivated too strongly thereby.

As is common in biotechnical reactions, the pH-value of the reaction liquid must be kept in a range favorable for the enzymes; as a rule this is pH 4 to 7. For example, an automatic pH-titration with NaOH or KOH to pH 5.5 has proved to be advantageous. Depending upon the origin of the GO and CAT which is used (from mold fungi, bacteria, beef liver or the like) the most favorable pH-value may vary within the indicated limits. It may easily be determined by tests known to all those skilled in the art.

If the enzyme particles are inclined to rise and cake, the agitator reactor should be rinsed or wiped intermittently or continuously in order to avoid caking of the enzyme particles in the head room of the reactor. This may be done in an easy manner by partially or completely recycling the reaction liquid and by spraying it against the wall in the head room, for example through a perforated ring-shaped pipe. In addition, the fermentation liquid may be recycled with or without enzyme particles. It is preferred to recycle it without enzyme particles in order to protect the latter from undesired shearing force, by mounting a filter or a screen in front of the suction discharge pipe.

According to a preferred embodiment, the process according to the invention is carried out in a reactor which has in the lower part a screen-, membrane- or filter-covered suction device and a ring-shaped spraying device in the head room. The attached drawing shows an illustrative embodiment of such an aerated agitator reactor, where 1=reactor filling; 2=agitator motor; 3=agitator; 4=filter sheet; 5=jacket for temperature adjustment; 6=recycling pump; 7=ring-shaped pipe with spray nozzles; 8=aerating ring; 9=gas intake; 10=metal impact sheets to prevent co-rotation of the fermentation brooth; 11=pH-meter and automatic titration device; 12=three-way valve and outlet.

The filter-, membrane- or screen-covered suction device 4 in the fermentor bottom shown as an example in the drawing has also the advantage that the total reacted fermentation liquid may be pumped off after the finished reaction and may be led via the three-way valve to its further use, for example precipitation or the like. The particle-bound enzymes remain in the reactor. If desired, they may be desinfected, rinsed and used again without being taken out of the reactor.

The apparatus for carrying out the process according to the invention may, of course, be varied to meet particular requirements.

For example, clinging of the enzyme particles to the walls of the reactor head room may be prevented by mechanical wipers. If the enzyme particles are specifically very heavy and not inclined to float up and cling to the reactor walls, this device intended for keeping the reactor head walls free from clinging enzyme particles is, of course, not required.

The process according to the invention is preferably used for glucose oxidation to obtain glucono-δ-lactone, gluconate, gluconic acid and/or fructose. The process may be use for obtaining fructose by oxidizing glucose in mixtures of glucose and fructose (for example, invert sugar, isomerose). The formed gluconic acid or the formed gluconate may then be separated by precipitation (for example, as calcium gluconate) or by ion exchange from the remaining fructose in a considerably more simple way than the originally present glucose.

An important advantage of the process according to the present invention is that the enzyme particles will not be deactivated after only a few days, but will remain useful for months. With the process according to the present invention the danger of infection can also be reduced due to the low temperature unfavorable for growth of microorganisms. The total quantity of glucose reaction obtainable with one gram of commercial GO-CAT-mixture increases to 10 kg and more, and thus exceeds considerably the state of the art.

The following examples illustrate the present invention and will enable others skilled in the art to understand it more completely. It should be understood, however, that the invention is not limited solely to the particular examples given below.

EXAMPLE 1

1 kg of food-grade gelatine having a Bloom number of 80 was dissolved in 3 liters of deionized water by heating to 60° C., while stirring. While continuing to stir quickly, 60 ml of a 30% formaldehyde solution were added. After stirring for about 4 minutes more at 60° C. the mixture had gelled. It was allowed to stand for 24 hours at room temperature, then coarsely comminuted and dried on trays in a drying cabinet at 105° C. The dried particles were ground to the desired fineness and yielded the carrier particles for enzyme immobilization.

For the subsequent enzyme fixation the commercial glucose oxidase-catalase product sold under the trademark Glucox-R by the firm J. & E. Sturge, Great Britain, was used. It had a glucose oxidase activity of 1580 Sarett units per ml, and a catalase activity of 540 Baker units per ml. 100 ml of this product were stirred with 380 ml of water and 50 gm of the hardened gelatin described above, which had been ground to a particle size of 20 to 50 μm and screened. Then, 700 ml of acetone and 30 ml of 25% glutar-dialdehyde were admixed therewith. After shaking the mixture for two hours on a waterbath at 25° C., the resulting enzyme-containing particles were filtered off and rinsed carefully with distilled water. The activity of this composition was 1270 Sarett units and 405 Baker units per ml of applied Glucox-R.

The total quantity of immobilized enzyme composition thus obtained from immobilization of 100 ml of Glucox-R was charged into an aerated agitator reactor with 50 liters of substrate containing 5 kg of glucose and 5 kg of fructose. The contents of the reactor were aerated with 50 liters (at normal pressure) of air per minute through a perforated pipe and stirred with a blade agitator at 560 revolutions per minute. By automatic titration with 10% NaOH, the pH-value was kept constant on 5.5±0.1. The temperature of the contents of the reactor was kept at 2±1° C. Part of the fermentation liquid was pumped out continuously via the membrane-covered screen bottom of the reactor and recycled into the reactor by means of a perforated ring pipe in such a way that it was sprayed diagonally from above against the wall in the head room of the reactor. Clinging of enzyme particles floated up with the gas bubbles to the head room wall of the reactor was thereby avoided. After conversion of all the glucose into gluconate, the fermentation liquid was suctioned off via the membrane-covered discharge connection attached to the bottom of the reactor. The enzyme particles remaining in the reactor were admixed at 2° C. with 0.5% of a disinfecting agent sold under the trade name Jodonal by C. H. Boehringer Sohn, Ingelheim, Germany, which previously had been adjusted with NaOH to pH 5.0. Before the next glucose conversion run the enzyme particles were washed with water. The first reaction was finished after 12.2 hours. The subsequent runs gradually took longer and longer, but 200 batches could be run before the duration of the conversion had grown to about 24 hours. With 200 batches a total of 1000 kg of glucose were converted together with 100 ml of the originally used 100 ml of commercial glucose oxidase-catalase. Further conversions were entirely feasible because the enzyme particles still had about half of their original activity.

EXAMPLE 2

A commercial glucose oxidase-catalase product sold under the tradename Maxazym-GO-L-1500 by Gist-Brocades, Delft, Holland, was used. This composition had a glucose oxidase activity of 1520 Sarett units per ml and a catalase activity of 370 Baker units per ml. 100 ml of this product were stirred with 400 ml of distilled water and 8 gm of egg albumin and then 800 ml of isopropanol and 25 ml of 25% glutar-dialdehyde added to the solution, while stirring. After stirring the mixture for two hours more at 25° C., the fixed enzyme particles were separated by filtration and washed thoroughly with water. The activity of this immobilized enzyme composition was 860 Sarett units and 206 Baker units per ml of the originally used soluble enzyme.

The total enzyme quantity resulting from the immobilization of 100 ml of soluble GO-CAT was charged into an aerated agitator reactor with 50 liters of a 20% glucose solution. The reactor was aerated with 50 liters (at notmal pressure) of air per minute through a perforated ring pipe mounted closely above the bottom of the reactor, and stirred with a blade agitator at 500 revolutions per minute. By automatic titration with 10% KOH, the pH-value was kept constant on 6.0±0.1. The temperature of the contents of the reactor was kept constant at 8±1° C. Part of the fermentation liquid was pumped out through a membrane-covered screen at the bottom of the reactor and recycled into the reactor through a perforated ring pipe in such a way that it was sprayed diagonally from above against the inner wall of the reactor, whereby floating up and clinging of the enzyme particles to the wall was prevented. After the total quantity of glucose had been converted, the fermentation liquid was suctioned off through the membrane-covered screen at the bottom. The enzyme particles remaining in the reactor were admixed at 2° C. with a 0.5% solution of a disinfecting agent sold under the name Absonal by C. H. Boehringer Sohn, which has previously been adjusted to pH 5.0. Before starting the next glucose conversion run, the enzyme particles were washed with water. The first conversion was finished after 29.6 hours. After 100 runs, the required time for complete conversion of the glucose increased to 68 hours. By means of the 100 runs, carried out with the originally used 100 ml of commercial glucose-oxidase-catalase, a total of 1000 kg of glucose were converted.

Glucose Oxidase Activity

Determination of the GO activity was effected pursuant to the method described in First Suppl. Food Chem. Codex, 2nd Edition, pages 78–79, Editors: National Academy of Sciences, Washington, 1974. The activity is indicated in Sarret units.

Catalase Activity

Determination of the CAT activity was effected by the method described in First Suppl. Food Chem. Codex, 2nd Edition, pages 67–68, Editors: National Academy of Sciences, Washington, 1974. The activity is indicated in Baker units.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

I claim:

1. A process for enzymatic oxidation of glucose with an immobilized glycose oxidase-catalase composition, which comprises performing the oxidation at a temperature of $2\pm1°$ C. in a reaction medium with an immobilized glucose oxidase-catalase composition consising essentially of glucose oxidase and catalase bound to hardened gelatin with a particle size of 10 to 100 μm, said composition having catalase activity expressed in Baker units at least one-sixth of the glucose oxidase activity expressed in Sarett units and said composition being present in an amount sufficient to provide 500 to 5000 sarett units of glucose oxidase and 200–2000 Baker units of calatase per liter of reaction medium.

* * * * *